(12) United States Patent
Tyner et al.

(10) Patent No.: US 7,118,876 B2
(45) Date of Patent: Oct. 10, 2006

(54) ALTERED INTRACELLULAR LOCALIZATION OF BRK/SIK PROTEIN TYROSINE KINASE IN HUMAN PROSTATE TUMORS

(75) Inventors: Angela Tyner, Chicago, IL (US); Jason J. Derry, Aurora, IL (US)

(73) Assignee: The Board of Trustees of the Univeristy of Illinois, Urbana, IL (US)

( * ) Notice: Subject to any disclaimer, the term of this patent is extended or adjusted under 35 U.S.C. 154(b) by 647 days.

(21) Appl. No.: 10/341,232

(22) Filed: Jan. 13, 2003

(65) Prior Publication Data

US 2003/0148358 A1     Aug. 7, 2003

Related U.S. Application Data

(60) Provisional application No. 60/347,720, filed on Jan. 11, 2002.

(51) Int. Cl.
*G01N 33/574*     (2006.01)
(52) U.S. Cl. ................. 435/7.23; 435/7.21; 436/65
(58) Field of Classification Search ............. 435/7.23, 435/7.2, 7.21; 436/65; 530/350, 387.9, 530/389.7
See application file for complete search history.

(56) References Cited

OTHER PUBLICATIONS

Mitchell et al. (Oncogene. 2000; 19: 4273-4282).*
Lukong et al. (J. Biol. Chem. Nov. 18, 2005; 280 (46): 38639-38647).*
Derry et al. (Oncogene. 2003; 22: 4212-4220).*
Easty et al., "Loss of Expression of Receptor Tyrosine Kinase Family Genes PTK7 and SEK in Metastatic Melanoma" *Int. J. Cancer* 71:1061-65 (1997).
Gleason et al., "Prediction of Prognosis for Prostatic Adenocarcinoma by Combined Histological Grading and Clinical Staging" *The Journal of Urology* 111:58-64 (1974).
Mitchell et al., "Cloning and characterization of cDNAs encoding a novel non-receptor tyrosine kinase, brk, expressed in human breast tumours" *Oncogene* 9:2383-2390 (1994).
Barker et al., "BRK tyrosine kinase expression in a high proportion of human breast carcinomas" *Oncogene* 15:799-805 (1997).
Lior et al., "BRK/Sik Expression in the Gastrointestinal Tract and in Colon Tumors" *Clin. Cancer Res.* 6:1767-77 (1999).
Lee et al., "A survey of protein tyrosine kinase mRNAs expressed in normal human melanocytes" *Oncogene* 8:3403-10 (1993).
Kasper et al., "Development, Progression, and Androgen-Dependence of Prostate Tumors in Probasin-Large T Antigen Transgenic Mice: A Model for Prostate Cancer" *Lab. Invest.* 78:319-333 (1998).
McNeal and Bostwick et al., "Intraductal Dysplasia: A Premalignant Lesion of the Prostate" *Hum. Pathol.* 17:64-71 (1986).
Qian et al., "The Extent and Multicentricity of High-Grade Prostatic Intraepithelial Neoplasia in Clinically Localized Prostatic Adenocarcinoma" *Hum. Pathol.* 28:143-8 (1997).
Kaighn et al., "Establishment and Characterized of a Human Prostatic Carcinoma Cell Line (PC-3)" *Invest. Urol.* 17:16-23 (1979).
Horoszewicz et al., "The LNCaP Cell Line-A New Model for Studies on Human Prostatic Carcinoma" *Prog. Clin. Biol. Res.* 37:115-21 (1980).
Lim et al., "Growth of an Androgen-Sensitive Human Prostate Cancer Cell Line, LNCaP, in Nude Mice" *Prostate* 22:109-18 (1993).
Vasioukhin et al., "A role for the epithelial-cell-specific tyrosine kinase Sik during keratinocyte differentiation" Proc. Natl. Acad. 94:14477-82 (1997).
Derry et al., "Sik (BRK) Phosphorylates Sam68 in the Nucleus and Negatively Regulates Its RNA Binding Ability" *Molecular and Cellular Biology* 20(16)6114-26 (2000).

* cited by examiner

*Primary Examiner*—Stephen L. Rawlings
(74) *Attorney, Agent, or Firm*—McDonnell Boehnen Hulbert & Berghoff LLP (57) ABSTRACT

The invention provides methods for detecting abnormal prostate conditions, such as benign prostatic hyperplasia (BPH), prostatic intraepithelial neoplasia (PIN), and adenocarcinoma, in an animal by comparing the amount of the Breast Tumor Kinase (BRK) tyrosine kinase in the nuclei of prostate luminal epithelial cells in a test sample with an amount of nuclear BRK protein in epithelial cells of normal prostate glands.

8 Claims, 8 Drawing Sheets

BPH

PIN

SAM68

B

Gleason 4

PIN

LNCaP PC3

Figure 8

ALTERED INTRACELLULAR LOCALIZATION OF BRK/SIK PROTEIN TYROSINE KINASE IN HUMAN PROSTATE TUMORS

This application is related to U.S. provisional application Ser. No. 60/347,720, filed Jan. 11, 2002.

This invention was made with government support under DK44525 and DK068503 awarded by the National Institutes of Health. The government has certain rights in the invention.

FIELD OF THE INVENTION

The invention relates to methods for detecting an abnormal prostate condition in an animal. Specifically, the invention relates to methods of detecting an abnormal prostate condition in an animal by detecting the amount of Breast Tumor Kinase (BRK) protein present in the nuclei of prostate luminal epithelial cells within a prostate tissue sample compared with the amount of BRK protein in the nuclei of normal prostate luminal epithelial cells. The invention further relates to methods for detecting prostate cancer in an animal by identifying prostate tissue samples wherein luminal epithelial cells in the sample do not display BRK nuclear localization.

BACKGROUND OF THE INVENTION

The estimated incidence of prostate cancer in men over the age of 50 is 30%, making it the most common form of cancer among males. Currently, prostate cancer is the second leading cause of cancer death among men in the United States.

Although a considerable amount of research has been devoted to developing effective therapies against the disease, prostate cancer remains difficult to treat. The most common forms of treatment remain based on surgery, radiation therapy, or a combination of surgery and radiation therapy. However, these methods are ineffective in a significant number of cases and have a great many deleterious side effects.

Two previously identified prostate specific proteins, prostate specific antigen (PSA) and prostatic acid phosphatase (PAP), have been identified and used as markers for identifying patients with or at risk for prostate cancer. The therapeutic and diagnostic potential of PSA and PAP, however, is limited. For example, PSA levels do not always correlate with the presence of prostate cancer. In some cases, elevated PSA levels are associated with a number of non-prostate cancer disorders, including benign prostatic hyperplasia (BPH). Furthermore, PSA measurements correlate with prostate volume, an unreliable marker for prostate cancer, and do not indicate the level of metastasis.

Besides serum markers, such as PSA, physicians recommend the digital rectal examination (DRE) for aging men, particularly men over the age of 50 or who have a family history of prostate cancer. The sensitivity of the DRE is limited, because the examining finger can only palpate the posterior and lateral portions of the gland, leaving some tumors undetected. If a DRE or serum marker test is abnormal, imaging tools, such as MRI or transrectal ultrasound must be used to further examine the gland. However, cancer is confirmed only by a biopsy.

Pathologists in the United States primarily use the Gleason system to assign as grade to tumors detected in biopsies. The Gleason system involves histologic grading based on the pattern of glandular formation, assigning a number of 1 to 5. Lower numbers are well differentiated and higher numbers are poorly differentiated (Gleason and Mellinger, 1974, *J. Urol.* 111:58–64). A pathologist assigns one number based on the level of differentiation of the most prevalent grade in the sample, and makes a second assessment based on the predominant secondary grade. The two grades are added together to get the "Gleason sum." While the Gleason system is widely used, it often leads to variable scores between different diagnosticians. Poor reproducibility between diagnosticians is a major problem in grading prostate tumors.

The screening methods for detecting and diagnosing prostate tumors discussed above are limited in their sensitivity. Consequently, there is a need in the art for improved methods of diagnosing prostate cancer. Given the discrepancy between pathologists in grading the severity of tumors, there also remains a need for an easier, more accurate method of grading prostate tumors.

SUMMARY OF THE INVENTION

The invention provides a method of diagnosing an abnormal prostate condition in an animal comprising the steps of: (a) assaying prostate tissue from the animal to determine how much Breast Tumor Kinase (BRK) protein is located in nuclei of epithelial cells comprising the prostate tissue sample; (b) assaying normal prostate tissue from the animal to determine how much BRK protein is located in the nuclei of epithelial cells comprising the normal prostate tissue; and (c) comparing the amount of BRK protein in nuclei of epithelial cells from the tissue sample in step (a) with the amount of BRK protein in nuclei of epithelial cells from the normal prostate tissue in step (b), wherein an abnormal prostate is identified if the amount of BRK protein in nuclei of epithelial cells from step (a) is less than the amount of BRK protein in the nuclei of epithelial cells from step (b). An abnormal prostate can be a prostate having, for example, an adenocarcinoma, a benign prostatic hyperplasia (BPH), or prostatic intraepithelial neoplasia (PIN).

In one aspect of the invention, the method further comprises the steps of: (d) selecting a portion of a tissue sample from an abnormal prostate as identified in step (c) above; and (e) histologically examining the tissue sample portion from step (d) to distinguish between a benign and malignant tumor, wherein the sample is identified as having prostate cancer if the tissue sample portion displays adenocarcinoma morphology.

In further aspects of the invention, a non-pathologist can determine the localization of BRK protein in the sample and select the samples having no nuclear staining of BRK, while a pathologist or someone with more advanced training can analyze the morphology of the tissue samples.

In another aspect, the inventive method can be used, for example, for pre-screening biopsies to determine if further analysis by a pathologist is necessary. A non-pathologist, such as a technician, can cost effectively perform a method of the invention and select candidate samples that require further analysis by a pathologist.

The invention further provides a kit for detecting prostate cancer in an animal comprising a BRK protein-specific reagent, such as polyclonal antisera or a monoclonal antibody and instructions for use.

Specific preferred embodiments of the invention will become evident from the following more detailed description of certain preferred embodiments and the claims.

DETAILED DESCRIPTION OF CERTAIN PREFERRED EMBODIMENTS

The invention relates to methods for diagnosing abnormal prostate conditions, including prostate cancer, using a diagnostic marker therefor. The diagnostic marker, BRK (breast tumor kinase), is a cellular protein the expression of which has been differentially detected in a wide variety of different tumors from a variety of cell types. The gene encoding this protein was cloned from a human metastatic breast tumor in a screen for protein tyrosine kinases involved in breast cancer (Mitchell et al., 1994, *Oncogene* 9:2383–2390). BRK has been found to be expressed in many breast carcinoma cell lines and in a high percentage of primary breast tumors that have been examined, but it has not been detected in normal breast tissue (Barker et al., 1997, *Oncogene* 15:799–805; Mitchell et al., 1994, *Oncogene* 9:2383–2390), or at any stage of mammary gland differentiation in the mouse (Llor et al., 1999, *Clin. Cancer Res.* 5:1767–77). BRK was also cloned from cultured human melanocytes and designated PTK6 (Lee et al., 1993, *Oncogene* 8:3403–10), and was subsequently found to be expressed in metastatic melanoma cell lines but not in normal melanocytes (Easty et al., 1997, *Int. J. Cancer* 71:1061–5). Moderate increases in BRK levels have also been detected in colon tumors (Llor et al., 1999, *Clin. Cancer Res.* 5:1767–77).

In contrast to carcinomas of the breast, skin, and colon, wherein BRK is more highly expressed than in normal breast, skin, and colon epithelial cells, BRK expression shows a different expression pattern between abnormal and normal prostate tissues. Surprisingly, as disclosed herein BRK protein localizes in the nuclei of prostate epithelial cells in normal prostate tissue, and BRK protein expression is reduced in the nuclei of epithelial cells in abnormal prostate tissue. For example, BRK protein was localized in the nuclei of epithelial cells in 70% of prostate tissue samples from patients with benign prostatic hyperplasia (BPH), while in 30% of the BPH patients BRK was localized in both the cytoplasm and the nuclei within the glands displaying BPH. Although the pattern of BRK localization in malignant prostate tumors varied with the severity of the tumor grade (predominantly but not entirely nuclear in the low grades and predominantly and in some cases entirely cytoplasmic in the high grades), abnormal prostate tissue was associated with a change (decrease) in nuclear localization of BRK protein.

These observations suggested that assays to determine the amount of BRK protein in the nuclei of epithelial cells in a prostate from an animal could be used to diagnose an abnormal prostate condition.

The phrase "abnormal prostate condition" as used herein refers to any histological or functional characteristic that differs from a normal histological or functional characteristic. For example, an abnormal prostate condition can be, for example, an adenocarcinoma, a benign prostatic hyperplasia (BPH), or prostatic intraepithelial neoplasia (PIN).

As used herein, an "animal" is preferably a mammal, such as a rodent or a primate. Preferably, an animal is a human.

A "non-pathologist" can be anyone who is not a trained pathologist, for example, a laboratory technician.

As used herein, "intensity" and "amount" of BRK nuclear staining are used interchangeably.

As discussed in the Examples below, 58 individual paraffin embedded human prostate surgical samples, having normal, benign, pre-neoplastic, malignant glands, or a combination of these conditions, were stained with anti-BRK antibodies. Sections from each surgical sample were stained with anti-BRK antibodies and analyzed by light microscopy.

The intensity of BRK nuclear staining was given a score on a scale from 1 to 100%, with 100% representing the intensity as displayed in the normal glands, since they displayed uniform intensity throughout their luminal epithelial cells, and 1% representing the absence of BRK nuclear staining. Glands with BRK nuclear staining similar to that seen in the nuclei of normal prostate epithelial cells were assigned two plus signs (++). Glands with approximately 75% the intensity of nuclear staining found in normal glands were assigned a (+), those with approximately 50% were assigned a (+/−), and those with 25% or less BRK positive nuclei were assigned a (−). The patterns of BRK expression observed in the 58 surgical samples are represented in Table 1 in the Examples below.

The only tissue samples examined that comprised epithelial cells in which BRK nuclear staining was undetectable by immunohistochemistry were prostatic adenocarcinomas (i.e., prostate cancer). Therefore, in one embodiment, the invention provides methods for detecting prostate cancer in an animal comprising the step of detecting localization of BRK protein in luminal epithelial cells in a prostate tissue sample from the animal, wherein the animal is identified as having prostate cancer if BRK protein is present primarily in the cytoplasm and undetectable by immunohistochemistry in the nuclei of some prostate luminal epithelial cells. As discussed herein, BRK localization is nuclear in prostate tissues having normal glands and a majority of prostate tissues having benign hyperplasia. Consequently, if a prostate tissue sample displays greatly decreased BRK localization in the nuclei of the glandular epithelial cells, the gland is identified as malignant, and non-malignant if BRK is expressed in epithelial cell nuclei in closer to normal amounts.

In another embodiment, the invention provides a method of detecting an abnormal prostate condition in an animal comprising the steps of: assaying a prostate tissue from the animal to determine how much Breast Tumor Kinase (BRK) protein is located in nuclei of epithelial cells within the animal prostate tissue; assaying a control prostate tissue from the animal to determine how much BRK protein is located in the nuclei of epithelial cell within the control prostate tissue; and comparing the amount of BRK protein in the nuclei of epithelial cells in step (a) with the amount of BRK protein in the nuclei of epithelial cells in step (b), wherein an abnormal prostate is identified if the amount of BRK protein in the nuclei of epithelial cells from step (a) is less than the amount of BRK protein in the nuclei of epithelial cells from step (b).

In certain embodiments, a non-pathologist can stain a prostate sample with a BRK-specific reagent, such as an anti-BRK antibody or antisera and determine the amount of BRK nuclear staining compared with the amount of BRK nuclear staining in a normal prostate gland, assigning the sample a grade of ++, +, +/−, or −. A grade of +, +/−, or − are can be further analyzed to distinguish between benign, malignant, and pre-malignant conditions, for example, by a pathologist who can histologically grade the samples or using various markers of specific prostate conditions. Given the histological heterogeneity of prostate tumors as discussed herein, a control sample used in the methods of the invention can be a normal prostate gland found within the sample that is being screened for an abnormal prostate condition, or the control can be obtained from a different animal having normal prostate glands.

A prostate tissue sample can be obtained, for example, by needle biopsy, in which a thin needle is guided through the rectum into the prostate, or by resection during surgery. Generally, needle biopsies comprise taking six to twelve samples from suspicious areas of the prostate located by sonography or from random areas to provide a general sampling. Tissue samples may be fixed in an appropriate histological fixative or analyzed fresh.

Localization of BRK protein in a tissue sample can be detected by immunohistochemical techniques, which are described, for example, in Harlow and Lane, 1998, USING ANTIBODIES: A LABORATORY MANUAL, Cold Spring Harbor Laboratory Press, New York. While any of several immunohistochemistry protocols can be used to determine BRK localization in a prostate tissue sample, the use of an antigen retrieval protocol prior to staining with anti-BRK antibodies is advantageously described in the Examples below. In addition, localization of BRK protein is more easily observed upon using an amplification procedure, such as that described in the Examples below. The BRK signal can be detected by fluorescence using, for example, fluorescent tags such as fluorescein isothiocyanate (FITC). Alternatively, BRK signal can be detected by light microscopy using, for example, a peroxidase substrate such as 3,3'-diaminobenzidine tetrahydrochloride dihydrate (DAB). When using a substrate such as DAB, the tissue sample can also be counterstained using an appropriate histological stain, such as hematoxylin, to visualize histological characteristics of the tissue.

When the amount of nuclear BRK protein is less in the test sample than in a normal control sample, the gland is identified as abnormal. The gland can then be further assessed to determine if the abnormal condition is benign, malignant, or pre-malignant. For example, the sample can be subjected to histological analysis to determine if the gland displays morphologic characteristics of a benign or malignant tumor.

When nuclear localization of BRK protein is 25–50% of the amount of nuclear BRK staining in normal prostate, the sample is identified as having BPH, adenocarcinoma, or a prostatic intraepithelial neoplasia (PIN). High grade PIN is a preinvasive stage of prostate cancer (Kaspar et al., 1998, Lab. Invest. 78:319–333; and Garabedian et al., 1998, Proc. Natl. Acad. Sci. USA 95:15382–87). PIN is found in prostate glands that also have cancer in more than 85% of cases (McNeal and Bostwick, 1986, Hum. Pathol. 17:64–71; and Qian et al., 1997, Hum. Pathol. 28:143–8).

Distinguishing between PIN and adenocarcinoma and BPH can be accomplished, for example, by observing certain morphologic characteristics that are associated with these tissues, such as the presence of a basement membrane surrounding the gland, which is present in PIN but absent in advanced adenocarcinoma. Since PIN is strongly predictive of adenocarcinoma, identifying PIN in a patient is clinically advantageous, resulting in more aggressive treatment that could prevent manifestation of cancer, for example, by surgical removal of the prostate or chemopreventive therapies.

Upon determining if a prostate tissue sample comprises BPH, PIN, or adenocarcinoma, a physician can prescribe an appropriate treatment protocol. In one embodiment of the invention, a physician can prescribe an appropriate treatment method based on the intensity of BRK nuclear staining. For example, a more radical treatment, such as surgery, may be necessary if BRK protein is not detected in the nuclei of epithelial cells in samples, whereas faint cytoplasmic staining of BRK accompanied by some nuclear staining of BRK might warrant careful monitoring of prostate growth in combination with non-surgical methods of treating prostate cancer, such as hormone therapy.

In another embodiment, the invention provides kits for detecting abnormal prostate conditions, such as BPH, adenocarcinoma, and PIN, comprising reagents that recognize BRK protein in a cell and instructions for using the reagents to detect the abnormal conditions. Preferably, a reagent that recognizes BRK protein is an anti-BRK antibody. The instructions for use will correspond to the methods described herein.

One of skill in the art will understand that prostate tumors are histologically heterogeneous, often comprising many normal glands and several varying grades of tumor within the same tissue. Therefore, while a particular gland might be normal in a tissue sample, other glands surrounding the normal gland might display abnormal characteristics. Thus, more then one gland within a prostate tissue sample should be considered before identifying the patient as having or not having an abnormal prostate condition.

EXAMPLES

The following examples, including the experiments conducted and results achieved are provided for illustrative purposes only and are not to be construed as limiting the invention.

Example 1

Figure 1:
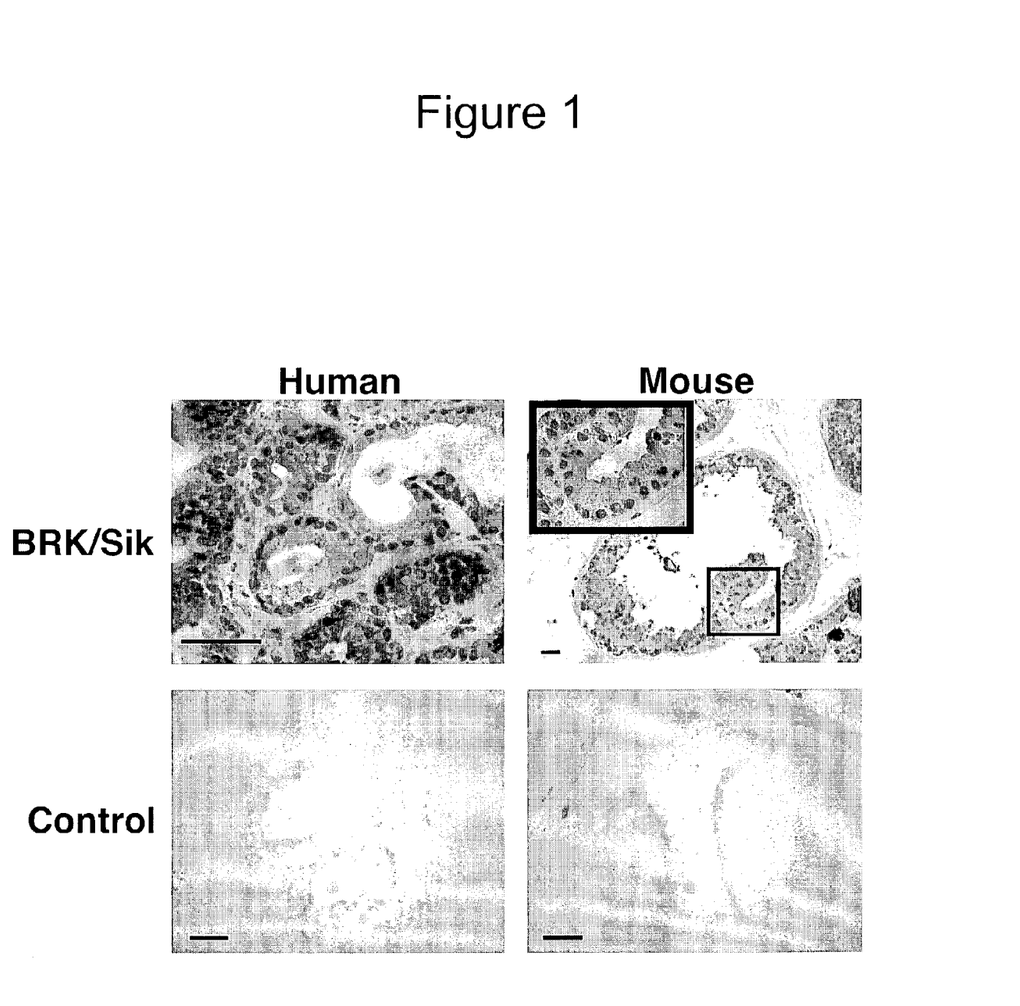
FIG. 1 depicts BRK nuclear expression (left panel) in normal human prostate tissue and the mouse ortholog of BRK (Src-related intestinal kinase; Sik) nuclear expression (right panel) in normal mouse prostate tissue as detected by immunohistochemistry. The inset on upper right panel is a higher magnification and shows Sik in the nuclei of the luminal epithelial cells. As controls parallel sections were incubated with rabbit IgG (lower panels) and no specific signal was observed. The size bar represents 50 µm.

BRK expression in the nuclei of normal human and mouse prostate secretory epithelial cells Expression of breast tumor kinase (BRK) and its mouse ortholog, Sik, was examined in sections of adult human and mouse prostate, respectively, using immunohistochemistry (FIG. 1). Ventral mouse prostates were surgically removed, fixed in 4% paraformaldehyde in phosphate buffered saline (PBS) overnight at 4°C., and washed in 70% ethanol. The tissues were then processed for paraffin embedding by passage through 70% ethanol for 1 hour (two times), 95% ethanol for 1 hour (three times), 100% ethanol for 1 hour (three times), xylene for 1 hour (two times), and liquid paraffin embedding medium (Fisher Scientific) at 62°C. for 1 hour (two times). The tissues were then mounted in paraffin blocks. Human prostate tissue samples were prospectively collected at the time of surgery for radical prostatectomy at Michael Reese Hospital, Chicago, Ill., in accordance with IRB guidelines, and embedded in paraffin blocks using standard embedding techniques.

Inmunohistochemistry was performed as described in Llor et al. (Llor et al., 1999, *Clin. Cancer Res.* 5:1767–77) using the TSA-Indirect Kit from Dupont/NEN (Boston, Mass.). Antigen retrieval was performed on hydrated paraffin sections of mouse or human tissue by microwaving in 1 mM EDTA pH 8.0 on high power three times for 5 minutes each or treatment with proteolytic enzymes according to manufacturer's instructions (Auto/Zyme, Vector, Burlingame, Calif.). Sections were incubated in block buffer with anti-Sik or anti-BRK polyclonal antibodies (Santa Cruz Biotechnology, Santa Cruz Calif.) (dilutions from 1:200–1:1000) overnight at 4°C. Controls included incubation with equal dilutions of rabbit IgG (or buffer alone. Signals were visualized with DAB (Vector Laboratories, Burlingame, Calif.) and analyzed by light microscopy.

Striking BRK and Sik expression was detected in nuclei of luminal prostate epithelial cells. The prostate is the first tissue where significant BRK/Sik nuclear localization was detected. The nuclear localization of BRK/Sik is significant, since a nuclear substrate, Sam68, which is phosphorylated by BRK/Sik, was previously described (Derry et al., 2000, *Mol. Cell Biol.* 20:6114–6126).

Example 2

BRK localization is altered in poorly differentiated prostate tumors

Fifty-eight individual paraffin embedded human prostate surgical samples were graded according to Gleason's microscopic grading system by a board-certified pathologist. Gleason's system involves histologic grading based on the pattern of glandular formation, assigning a number of 1 to 5. Lower numbers are well differentiated and higher numbers are poorly differentiated (Gleason & Mellinger, 1974, *J. Urol.* 111:58–64). Among the samples examined, normal, benign, preneoplastic, and malignant conditions were observed. Sections from each surgical sample were stained with anti-BRK antibodies and two individuals analyzed the sections by scoring at least three fields per slide using light microscopy. The intensity of BRK nuclear staining was given a score on a scale from 1 to 100%, with 100% representing the intensity as displayed in the normal glands, since they displayed uniform intensity throughout their luminal epithelial cells, and 1% representing undetectable BRK nuclear staining, as determined by immunohistochemistry. Glands with BRK nuclear staining similar to that seen in the nuclei of normal prostate epithelial cells were assigned two plus signs (++). Glands with approximately 75% the intensity of nuclear staining found in normal glands were assigned a (+), those with approximately 50% were assigned a (+/−), and those with 25% or less BRK positive nuclei were assigned a (−). The patterns of BRK expression that were observed in the 58 surgical samples are summarized in Table 1.

TABLE 1

| Nuclear Localization of BRK | | | | | |
|---|---|---|---|---|---|
| | ++ | + | +/− | − | Total Number of Samples |
| Normal | 100% | | | | 21 |
| BPH | 70% | | 30% | | 20 |
| PIN | | | 100% | | 7 |
| Grade 2–3 | | 60% | | 40% | 5 |
| Grade 4–5 | | | 60% | 40% | 5 |

Figure 2:
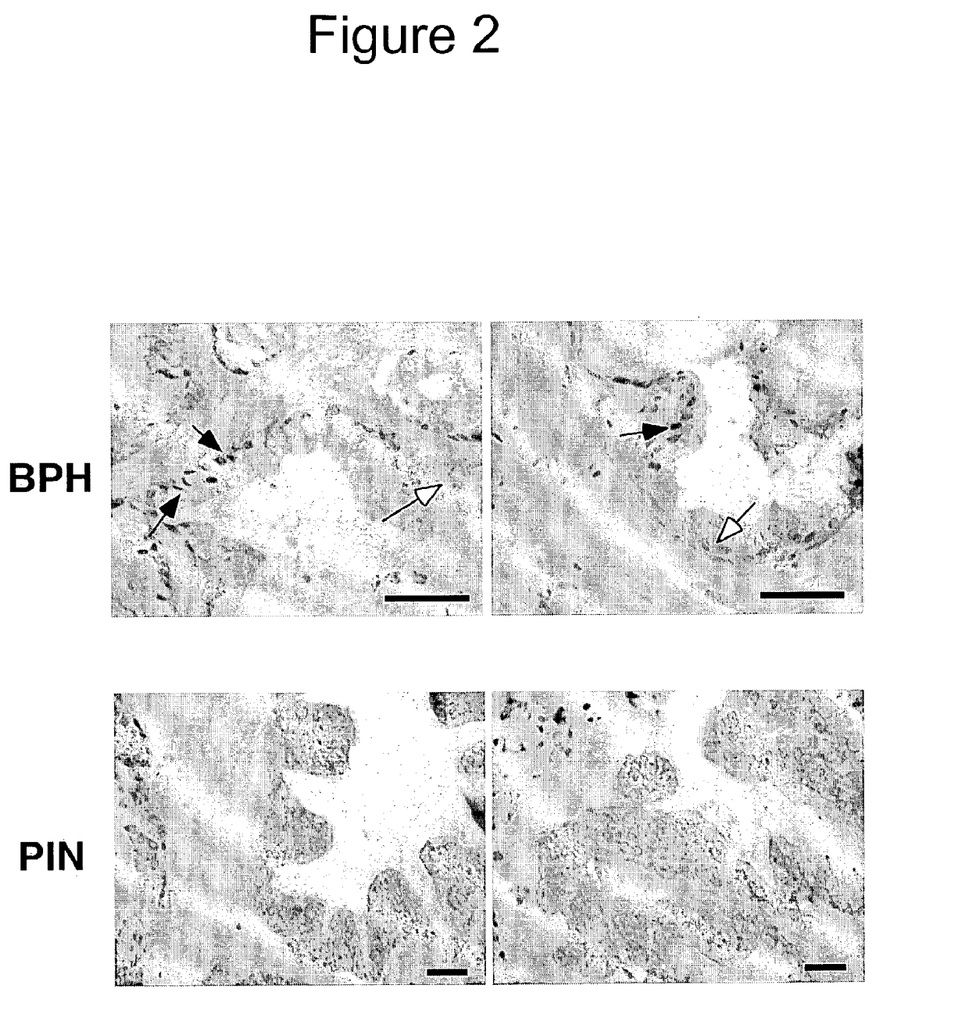
FIG. 2 depicts BRK expression in benign prostatic hyperplasia and prostatic intraepithelial neoplasia as detected by immunohistochemistry. Top panels show benign prostatic hyperplasia (BPH), with black arrows indicating nuclear staining, and white arrows directed at epithelial cells with faint or absent nuclear staining. Portions of the BPH glands retain nuclear BRK (top panels), while nuclei are devoid of BRK staining in prostatic intraepithelial neoplasia (PIN; bottom panels). The size bar represents 100 µm.

Nuclear expression of BRK was a hallmark of normal glands and in 70% of benign prostatic hyperplasia (BPH). Intense staining of the nuclei was also detected in one gland undergoing atrophy resulting from normal aging and in another normal condition known as transitional cell metaplasia. Nuclear expression of BRK was not observed in any of the glands with prostatic intraepithelial neoplasia (PIN), considered a precancerous condition. Typical nuclear staining in BPH tissues and the lack of nuclear staining of PIN tissues is shown in FIG. 2.

Figure 3:
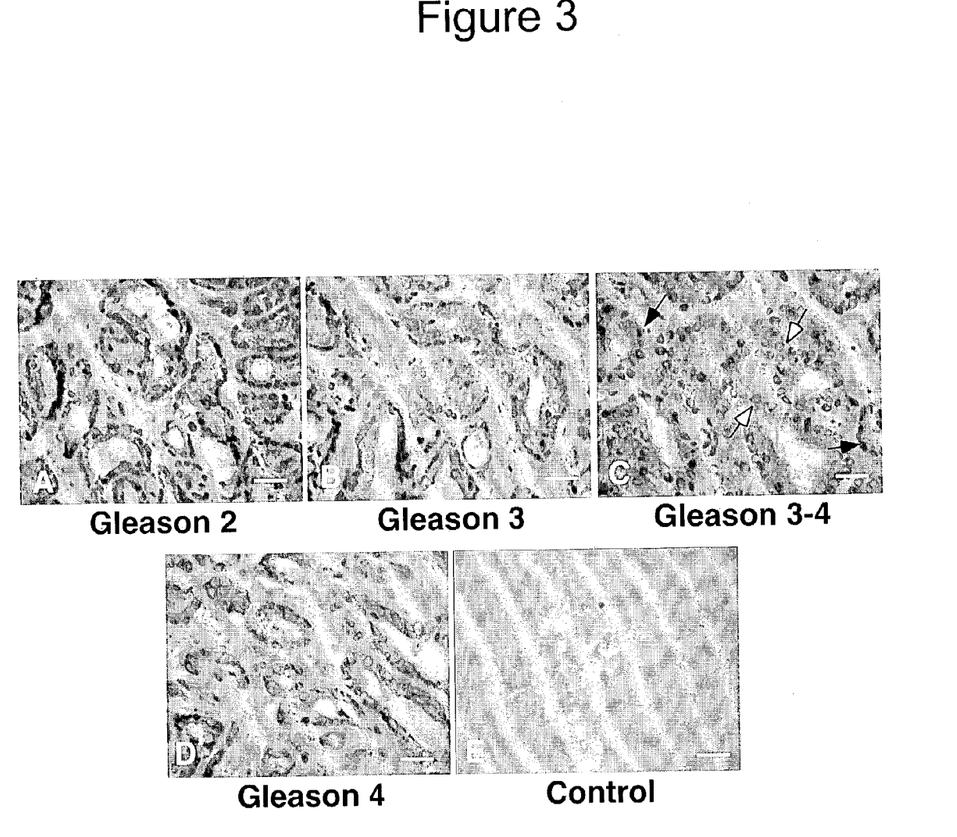
FIG. 3 depicts localization of BRK in poorly differentiated prostate tumors as detected by immunohistochemistry. (A) BRK is localized to nuclei in a well-differentiated tumor, although staining is less intense than in normal glands. (B) A Gleason 3 gland with nuclear staining less intense than staining in Gleason 2. (C) Gleason 3 glands merging into Gleason 4. A few nuclei are staining positive in the Gleason 3 glands (black arrows), while most are staining in a perinuclear pattern (white arrows). Cells in the Gleason 4 gland also have a perinuclear staining that is less intense. (D) A Gleason 4 gland with no nuclei positive for BRK staining. (E) Control incubated with rabbit IgG. Size bars represent 50 µm.
Figure 4:
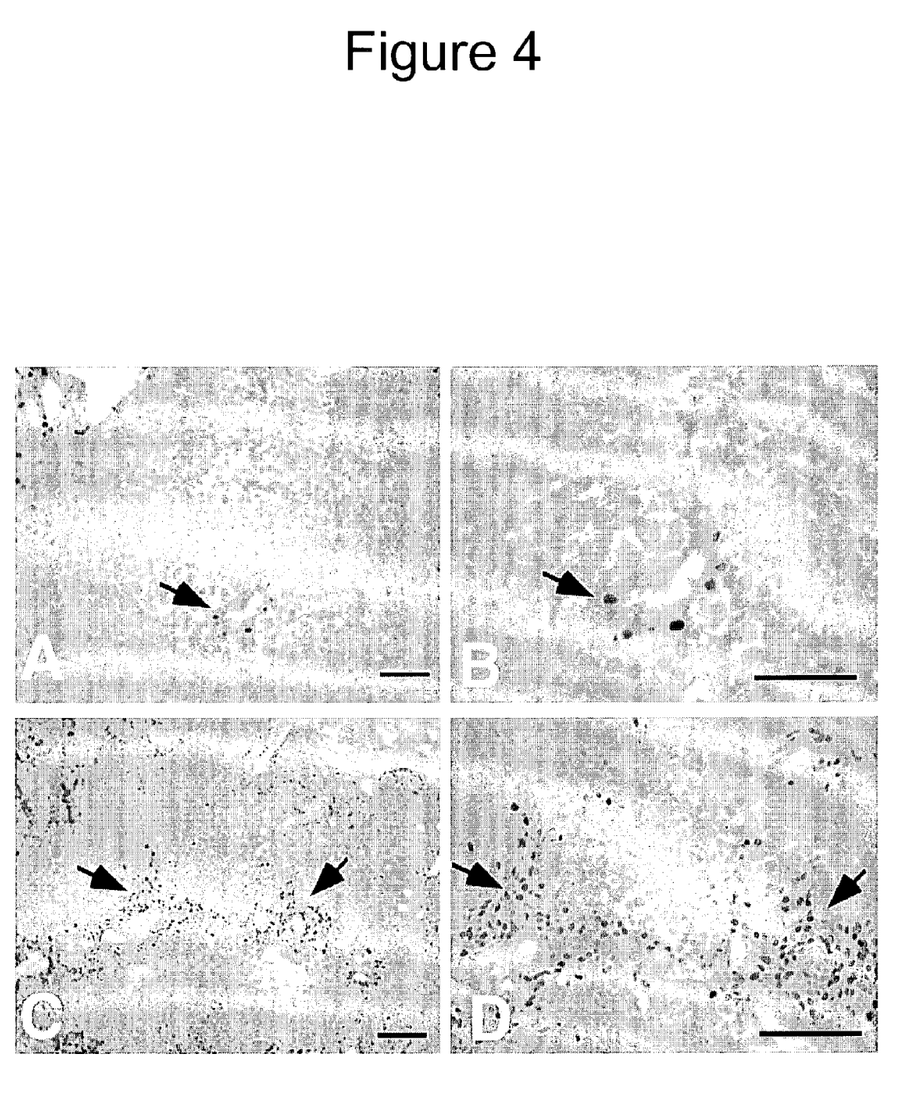
FIGS. 4A and 4C depict a Gleason 4 prostate tumor stained with anti-BRK antibodies. A sheet of poorly differentiated epithelial cells, which lack nuclear expression of BRK is shown surrounded by poorly differentiated glands. Some of the epithelial cells in the more differentiated regions that resemble glandular structures stain positively for BRK in the nuclei (arrows). Size bars represent 50 µm.
FIGS. 4B and 4D are higher magnifications of FIGS. 4A and 4C, respectively. Size bars represent 50 µm.

All grades of differentiation as determined by the Gleason scale were observed in the biopsies except Gleason grade 1. Some degree of BRK nuclear staining was observed in all grades, except grade 5. However, the intensity of the nuclear stain was much less than in normal tissues and this decreased with increasing grade (FIG. 3). FIG. 4 shows a Gleason grade 4 tumor with a few positively stained nuclei (arrows) surrounded by a sheet of epithelial cells with negatively stained nuclei. The BRK positive nuclei were in cells that appeared most differentiated within this tumor and resemble a poorly differentiated gland. Prostate tumors are histologically heterogeneous, consisting of many normal and several varying grades of tumor within the same tissue. Every normal gland observed adjacent to tumor glands was positive for BRK staining. Four of the tumors were negative for BRK staining in the nuclei of secretory epithelial cells.

To determine if the nuclear to cytoplasmic translocation of BRK occurred within cells of different pathologic states within a single patient, biopsy samples of a single patient with normal, BPH, PIN, and glands scored Gleason 2–4 were examined by immunohistochemistry as above. As expected, nuclei in epithelial cells of the normal and BPH glands were positive. PIN had no positive nuclei. While nuclear staining was observed in glands of Gleason 2, 3, and 4, the intensity of the stain decreased as the grade increased, supporting the data collected from samples from different individual patients.

Example 3

Localization of Sam68 is unaltered in high grade prostate tumors

Figure 5:
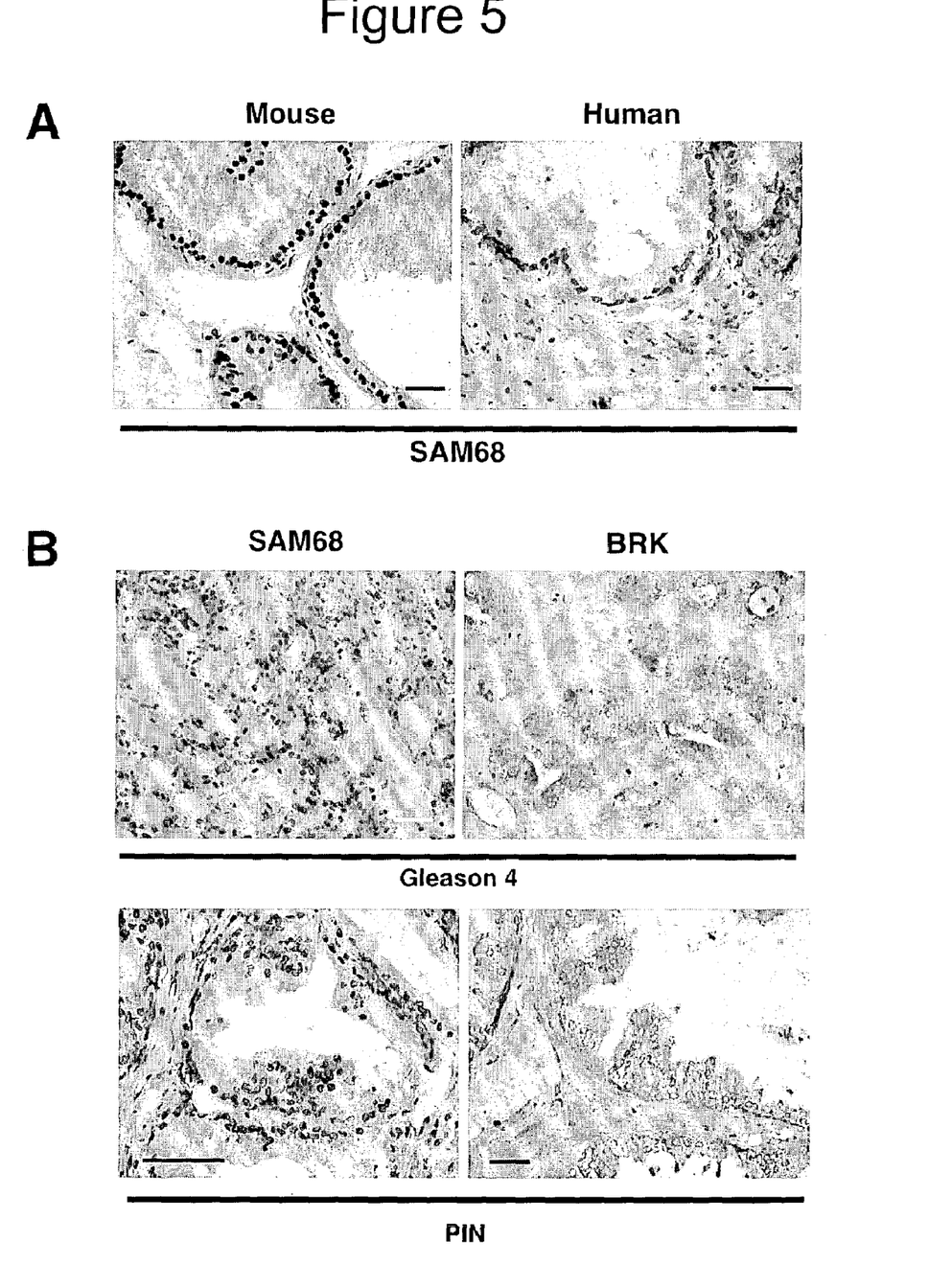
FIG. 5A depicts localization of the BRK substrate Sam68 in normal prostate glands of mouse and human prostates as detected by immunohistochemistry. Size bars represent 100 µm.
FIG. 5B depicts nuclear localization of Sam68 in human prostate tissue samples from a patient with a Gleason 4 tumor and a patient with PIN as detected by immunohistochemistry. Size bars represent 100 µm.

Since BRK localization changes as tumors dedifferentiate, the localization of Sam68, a substrate of BRK, was also examined to determine if the state of differentiation affected Sam68 localization. Sam68 was localized in human and mouse prostate using immunohistochemistry as described above. Sam68 was detected in nuclei of luminal epithelial cells in both human and mouse prostate (FIG. 5A). Sections from the same tumor tissue blocks used to study BRK localization above were stained with anti-Sam68 antibodies and examined by light microscopy. While BRK showed loss of nuclear localization in the less differentiated tumors, Sam68 localization was unchanged in the BPH, PIN, and tumor samples compared with its expression pattern in normal tissues. FIG. 5B shows Sam68 and BRK localization a Gleason grade 4 tumor and in PIN.

Example 4

Decreased BRK nuclear expression in the poorly differentiated PC3 human prostate tumor cell line BRK expression was also examined in two prostate tumor cell lines, LNCaP and PC3, and was compared with BRK expression in other human carcinoma cell lines, including HeLa cells, the MCF7 breast tumor cell line, and the HT29 and SW480 colon carcinoma cell lines. Cell lines were obtained from the American Type Culture Collection (ATCC). All cell lines were maintained in Dulbecco modified Eagle medium (DMEM) with 10% bovine calf serum except PC3 and LNCaP cells, which were maintained in RPMI with 10% bovine calf serum. Cultured cells were lysed as described in Vasioukhin and Tyner (1997, *Proc. Natl. Acad. Sci. USA* 94:14477–82). Samples were spun in a centrifuge for 10 minutes at 4° C. at 14000 rpm. Cell lysates were separated by SDS-PAGE and immunoblotting was performed as described in Vasioukhin and Tyner (1997, *Proc. Natl. Acad. Sci. USA* 94:14477–82) with anti-BRK antibodies.

Figure 6:
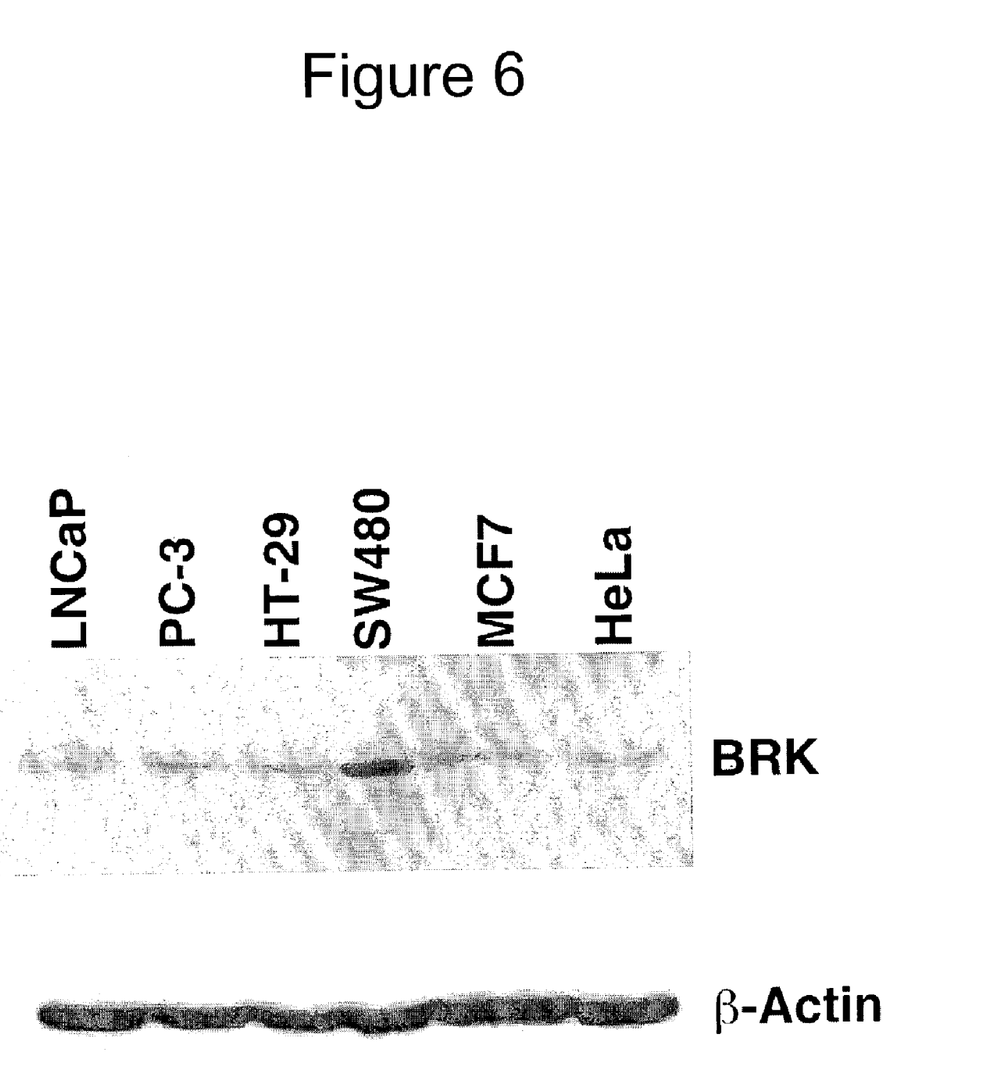
FIG. 6 depicts a Western blot analysis demonstrating BRK expression in carcinoma cell lines. Immunoblotting was performed with antibodies against BRK and β-actin, as a loading control.

BRK protein was detected in all of the human carcinoma cell lines (FIG. 6). A comparison of the two prostate cell lines, PC3 and LNCaP, indicated a slightly higher level of expression in the PC3 cells.

Figure 7:
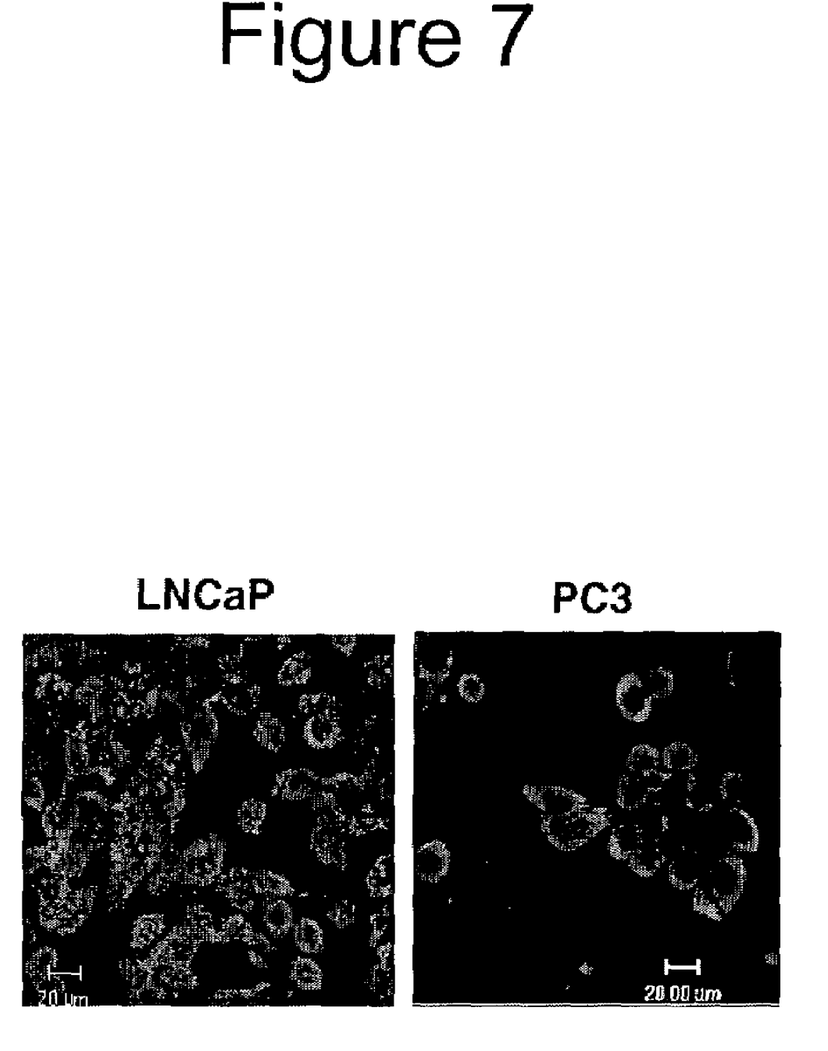
FIG. 7 depicts cells from LNCaP and PC3 prostate cancer cell lines stained with anti-BRK antibodies. BRK is present in the cytoplasm and in distinct nuclear structures in LNCaP cells (left panel), while it is present only in the cytoplasm of PC3 cells (right panel).

LNCaP and PC3 cell lines represent two different spectrums of prostate cancer. PC3 cells are highly aggressive and metastasize in nude mice. The cells also grow in the absence of androgens and are poorly differentiated (Kaighn et al., 1979, *Invest. Urol.* 17:16–23). In contrast LNCaP cells do not form metastatic tumors in nude mice, respond to androgens, and are well differentiated (Horoszewicz et al., 1980, *Prog. Clin. Biol. Res.* 37:115–32; Lim et al., 1993, *Prostate* 22:109–18). To determine if BRK localization was different in the LNCaP cell line compared with the PC3 cell line, the cells were grown on chamber slides and fixed in methanol at −20° C. for 5 minutes or Carnoy's fixative for 5 minutes at room temperature. The cells were then stained with anti-BRK antibodies as described in Derry et al. (2000, *Mol. Cell Biol.* 20:6114–6126). BRK antibody staining of cultured cells was visualized with rhodamine-avidin DAB (Vector Laboratories, Burlingame Calif.) (1:500). The results were analyzed by confocal microscopy. Endogenous BRK was detected throughout the cytoplasm as well as in distinct nuclear dots in LNCaP cells, while BRK staining was present in the cytoplasm but absent from the nuclei of PC3 cells (FIG. 7).

Sam68 and BRK co-localize in the nucleus of breast and colon carcinoma cell lines in Sam68/SLM nuclear bodies (SNBs) (Derry et al., 2000, *Mol. Cell Biol.* 20:6114–6126). Since BRK was localized in distinct dots in the LNCaP cells, the LNCaP cells were co-stained with BRK and Sam68 to determine if BRK was also localizing in SNBs in these cells. Co-staining was done as described in (Derry et al., 2000, *Mol. Cell Biol.* 20:6114–6126). Briefly, cells were stained with rabbit anti-BRK antibodies and rhodamine-avidin, as described above, followed by incubation with anti-Sam68 (BD Biosciences, San Jose, Calif.) (1:50) for 1 hour at room temperature and anti-mouse IgG FITC conjugate (Sigma, St. Louis Mo.) (1:64). Nuclei were stained with DAPI (Roche Applied Science, Indianapolis Ind.). Controls were performed by incubation with buffer alone, rabbit serum, or rabbit IgG before incubation with secondary antibody. The results indicated that BRK co-localized with Sam68 in the nuclei of LNCaP cells in SNBs.

Nuclear association of BRK and Sam68 in LNCaP cells was further confirmed by co-immunoprecipitation experiments. LNCaP and PC3 cells were harvested by centrifugation, washed 2 times with 1×PBS followed by one wash with hypotonic lysis buffer (HLB: 20 mM Tris-HCl pH7.5, 1 mM $MnCl_2$, 2 mM EGTA) for 5 minutes on ice. Cells were then covered with 1.5 ml HLB containing 20 ug/ul leupeptin and 1 mM PMSF per plate, scraped, and transferred to 15 ml tube and agitated on ice for 20–30 minutes. Cells were then homogenized in a Dounce homogenizer (50–60 strokes) and spun for 10 minutes at 2300 rpm at 4° C. to separate the nuclei. The pellet was washed in 1 ml of HLB and resuspended in 1 ml Dignum buffer (20 mM Hepes pH 7.9, 420 mM NaCl, 1.5 mM $MnCl_2$, 0.1 mM EDTA, 25% glycerol, 0.5 mM DTT, 0.5 mM PMSF, 2 ug/ml leupeptin, 2 ug/ml aprotinin, 1 mM $NaVO_4$). Nuclei were then agitated on a rotary shaker for 15 minutes at 4° C., spun for 10 minutes at 14000 rpm at 4° C. The supernatant was kept as the nuclear fraction.

Figure 8:
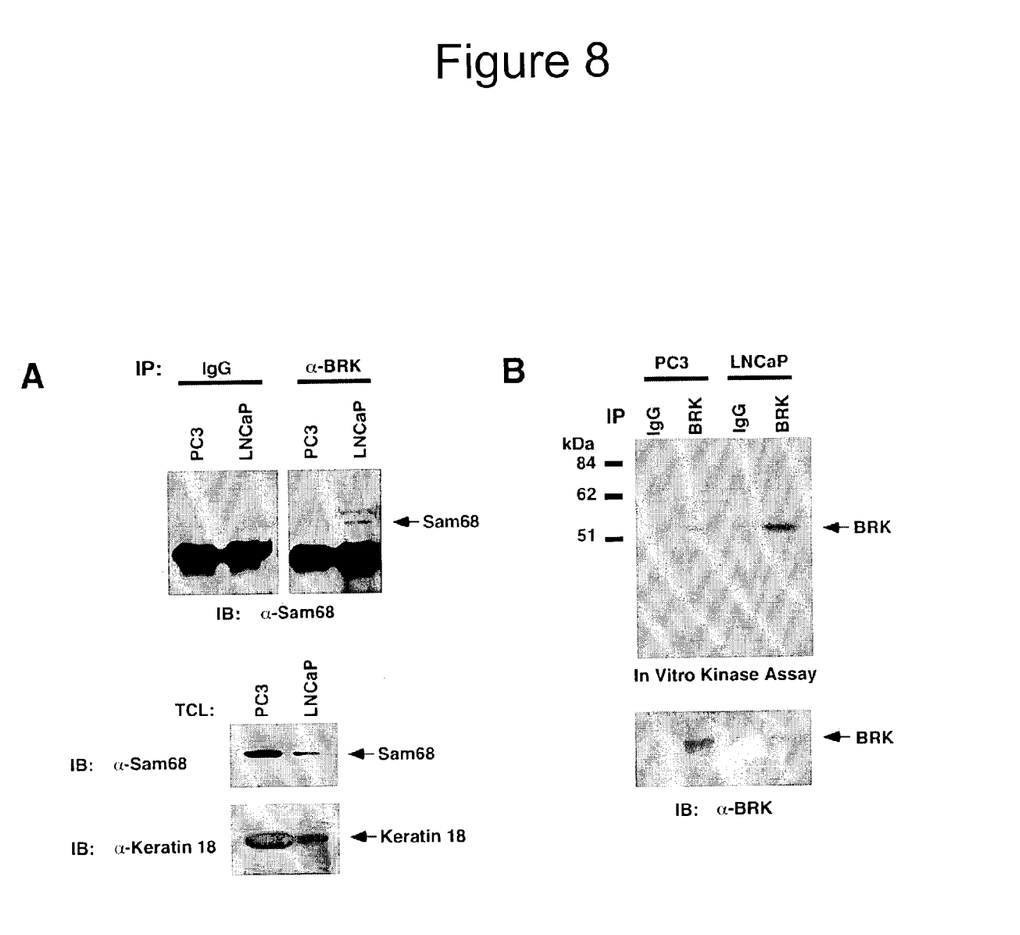
FIG. 8A depicts a Western blot showing that BRK co-immunoprecipitates with Sam68 in the nuclei of LNCaP cells. Immunoblotting performed with total cell lysates and anti-Sam68 antibodies demonstrates that Sam68 is expressed in both LNCaP and PC3 cells (lower panel). Keratin 18 expression was examined as a control for protein loading.
FIG. 8B depicts a kinase assay showing that BRK activity is higher in LNCaP cells than in PC3 cells. The lower panel shows anti-BRK antibody binding to same membrane and indicates the amount of BRK protein immunoprecipitated in the reaction.

Immunoprecipitations were performed with LNCaP and PC3 nuclear lysates and anti-BRK antibodies followed by immunoblotting with anti-Sam68 antibodies as described in (Derry et al., 2000, *Mol. Cell Biol.* 20:6114–6126). Lysates were immunoprecipitated with rabbit IgG as a control. A band corresponding to Sam68 was detected in the LNCaP nuclear fraction but not in the PC3 nuclear fraction (FIG. 9A). Immunoblotting was also performed with total cell lysates and anti-Sam68 antibodies to show endogenous expression of Sam68 in these prostate tumor cell lines and with anti-keratin 18 antibodies as a loading control.

The localization experiments in the prostate cancer cell lines closely parallel what was observed in the human tumor tissues, with nuclear localization being absent in the undifferentiated PC3 cells.

Example 5

BRK Activity in Prostate Cancer Cells Lines

To determine if altered localization of BRK might affect its activity, in vitro kinase assays were performed as described in Vasioukhin and Tyner (1997, *Proc. Natl. Acad. Sci. USA* 94:14477–82). Immunoprecipitations were performed with BRK antibodies and lysates from LNCaP and PC3 cells followed by incubation with [γ$^{32}$P]ATP and kinase buffer as described above. No exogenous substrate was used since BRK can undergo autophosphorylation. Proteins were resolved on SDS-PAGE and transferred to a nitrocellulose membrane that was exposed to film to detect phosphorylated proteins (FIG. 8B). Bands were detected in both samples migrating at the size of BRK. Immunoblotting was subsequently performed with the membrane and anti-BRK antibodies to confirm the identity of these bands and to control for the amount of protein present in the assay (FIG. 8B, bottom panel). Although a lower amount of BRK was immunoprecipitated from LNCaP cells, its activity was significantly higher suggesting that nuclear localization of the kinase may influence its activity.

It should be understood that the foregoing disclosure emphasizes certain specific embodiments of the invention and that all modifications or alternatives equivalent thereto are within the spirit and scope of the invention as set forth in the appended claims.

We claim:

1. A method of diagnosing an abnormal prostate condition in an animal, wherein the abnormal prostate condition is adenocarcinoma, benign prostatic hyperplasia (BPH), or prostatic intraepithelial neoplasia (PIN), the method comprising the steps of:

a. assaying a prostate tissue sample from the animal to determine how much Breast Tumor Kinase (BRK) protein is located in nuclei of epithelial cells within the animal prostate tissue;

b. assaying a normal prostate tissue sample from the animal to determine how much BRK protein is located in the nuclei of epithelial cell within the normal prostate tissue; and c. comparing the amount of BRK protein in the nuclei of epithelial cells from the prostate tissue sample in step (a) with the amount of BRK protein in the nuclei of epithelial cells from the normal prostate tissue sample in step (b), wherein an abnormal prostate having adenocarcinoma, benign prostatic hyperplasia (BPH), or prostatic intraepithelial neoplasia (PIN) is identified if the amount of BRK protein in the nuclei of epithelial cells from step (a) is less than the amount of BRK protein in the nuclei of epithelial cells from step (b).

2. The method of claim 1, wherein the animal is a mammal.

3. The method of claim 2, wherein the mammal is a human.

4. The method of claim 1, wherein the amount of BRK protein in the nuclei of epithelial cells in step (a) and the amount of BRK protein in the nuclei of epithelial cells in step (b) is determined by immunostaining.

5. The method of claim 1, further comprising the steps of:

d. selecting a portion of a tissue sample from an abnormal prostate as identified in step (c); and e. histologically examining the portion from step (d) to distinguish between a benign and malignant tumor, wherein the sample is identified as having prostate cancer if the portion displays adenocarcinoma morphology.

6. The method of claim 1, wherein the abnormal prostate condition is prostatic intraepithelial neoplasia (PIN).

7. The method of claim 1, wherein the abnormal prostate condition is benign prostatic hyperplasia (BPH).

8. The method of claim 1, wherein the abnormal prostate condition is adenocarcinoma.

* * * * *

UNITED STATES PATENT AND TRADEMARK OFFICE
CERTIFICATE OF CORRECTION

PATENT NO. : 7,118,876 B2 Page 1 of 1
APPLICATION NO. : 10/341232
DATED : October 10, 2006
INVENTOR(S) : Tyner et al.

It is certified that error appears in the above-identified patent and that said Letters Patent is hereby corrected as shown below:

At Column 1, line 9, please delete "and DK068503".

Signed and Sealed this

Seventh Day of August, 2007

JON W. DUDAS
*Director of the United States Patent and Trademark Office*